United States Patent [19]
Luce et al.

[11] Patent Number: 4,881,807
[45] Date of Patent: Nov. 21, 1989

[54] OPTICAL ALIGNMENT SYSTEM

[75] Inventors: David A. Luce, Clarence Center; Srdjan Krstanovic, Kenmore, both of N.Y.

[73] Assignee: Cambridge Instruments, Inc., Cheektowaga, N.Y.

[21] Appl. No.: 228,482

[22] Filed: Aug. 5, 1988

[51] Int. Cl.$^4$ .............................................. A61B 3/14
[52] U.S. Cl. ..................................... 351/208; 351/210
[58] Field of Search ............... 351/206, 208, 209, 210, 351/211; 354/62

[56] References Cited
U.S. PATENT DOCUMENTS
4,511,227 4/1985 Nunokawa et al. ................ 351/208
4,678,297 7/1987 Ishikawa et al. .................... 351/208

Primary Examiner—P. M. Dzierzynski
Attorney, Agent, or Firm—Bean, Kauffman & Spencer

[57] ABSTRACT

An optical alignment system using at least one CCD array for positioning an instrument in a chosen relationship to an object is disclosed. Means for "electronically" aligning the optical components and providing a macro view of the object on a CRT without additional illumination are also disclosed. Alignment may be achieved manually, if the operator observes the position of symbols on a CRT that move in response to movement of the instrument by the operator using a joystick, or automatically using information provided by the array.

27 Claims, 5 Drawing Sheets

OPTICAL ALIGNMENT SYSTEM

BACKGROUND OF THE INVENTION

It is frequently desirable to be able to repeatedly position an instrument, such as an ophthalmic instrument, in a predetermined spatial location relative to an object. For example, a non-contact tonometer must be carefully positioned relative to an eye under test in order to obtain an accurate intraocular pressure reading. It is desirable that the operator be able to position the instrument rapidly, since non-contact tonometers are frequently used to screen a large number of individuals for early warning signs of glaucoma by measuring their intraocular pressure. Instruments, such as non-contact tonometers, must be positioned not only relative to the eye laterally, but also spaced a proper distance axially from the eye. In such instruments, the patient normally places his forehead against a rest and his chin in a cup-like support. The operator then moves the instrument towards the eye to be tested, while observing various indicia until the predetermined location relative to the eye under test is achieved as indicated by the indicia.

The alignment system of the first commercial non-contact tonometer is disclosed in U.S. Pat. No. 3,756,073, issued Sept. 1973 to Lavallee et al. The optical system included a projected target, which the operator centered inside an aiming reticle by looking through an eyepiece, in order to obtain correct lateral positioning. The proper distance from the eye under examination was achieved by moving the instrument toward the patient's eye until the image of the reflected target was observed to be sharply focused. Since operator's were aware that they would not be able to observe the eye through the optical system during the alignment process, they usually performed an initial positioning of the instrument by observing the location of the instrument relative to the eye from the side, while moving the instrument into an approximated proper position. After approximated positioning, the operator then looked through the eyepiece to obtain accurate positioning of the instrument. This procedure avoided inadvertent contact with the eye. A light detector was used to verify the operator's correct alignment before testing.

The miniaturization of electronic components and particularly those relating to television, i.e., cameras and monitors, has permitted adaptation of earlier optical systems to permit the operator to observe the positioning indicia on a CRT screen. U.S. Pat. No. 4,665,923, issued May 19, 1987 is an example of such an alignment system and includes three optical subsystems. Two of the optical subsystems are symmetrically disposed about the instrument axis and provide visible indicia indicating the position of the instrument relative to a predetermined location. The third optical subsystem is used to provide the operator with a macro image of the eye. All of the embodiments disclosed in the patent, as well as the commercial product utilizing disclosed concepts, present the three images to a single observation means, i.e. image pickup tube 53. It is readily apparent that the patented system has the distinct disadvantage that proper adjustment can only be achieved by meticulous adjustment of each component of the two symmetrically disposed systems and manufacturing all components to close tolerances. For example, the first embodiment requires precise alignment of eight reflective surfaces in the two alignment optical subsystems, and even the simplest system, that shown in FIGS. 9 and 10, requires precision alignment of five reflective surfaces. Obviously, the dimensions of each component as well as the mounting thereof and spacing therebetween are extremely critical. An additional disadvantage of the disclosed optical systems is the requirement that at least four of the reflective elements be beam dividers. This substantially reduces the amount of original illumination that can be presented to the image pickup tube. A further disadvantage of the disclosed systems is that optically presenting three separate images to a single camera tube or CCD array causes the macro image of the eye to be washed out or at least very faint. Similar to the earlier system, a spot detector was used to verify correct alignment by the operator before testing in all of the disclosed embodiments.

The criticality in alignment is partly due to the use of a "spot" detector to verify alignment. It is only after light has passed through or been reflected by numerous elements that the spot or spots are evaluated to determine how much light is falling on the detector. introducing errors because of alignment or quality. Another factor affecting the system adversely is the quality of the optics required. Since the disclosed system projects a target image that is imaged on the observation means and the detector, the quality of the final images is controlled by the quality and alignment of all the intervening optical components.

U.S. Pat. No. 4,705,045, issued Nov. 10, 1987, discloses a tonometer alignment system having two oblique target projection systems that re-image the targets through an imaging optical system that is parallel to the discharge tube axis. Only imaging light that is reflected from the eye parallel to the imaging optical system axis is imaged on the detector, with both images being superimposed when the tonometer is aligned properly.

SUMMARY OF THE INVENTION AND BRIEF DESCRIPTION OF THE DRAWINGS

It is an object of the present invention to significantly reduce the number of optical elements requiring critical positioning in an optical alignment system. It is a further object of the present invention to provide an optical alignment system presenting a major portion of the initial illumination to the detector.

It is a still further object of the present invention to provide a clear image of the object relative to which the instrument is being aligned.

It is still another object of the present invention to provide an electronic alignment of an ophthalmic instrument.

A still further object of the present invention is to provide an alignment verification system that does not require additional detectors.

A still further object of the present invention is to provide a macro view of the eye without a light source in addition to that used for alignment.

It is a still further object of the present invention to automatically, i.e. electro-mechanically, align a test instrument using information provided by at least one CCD array.

Briefly, the present invention includes two light sources for reflecting spots from opposite sides of a spherical object, such as an eye. The reflected images are directed to at least one position sensitive detector, such as a CCD array. The signal produced by such a detector indicates the location of the image on the light sensitive area. Alignment of the optics may be achieved electronically by positioning the instrument in a predetermined location relative to the spherical object and storing the position of the spot as a reference location. The position of the instrument at any future time can then be presented relative to that stored reference location. Alternatively, the system can be aligned by moving each array normal to the light path until the spot is centered on both arrays when the instrument is properly positioned. In the latter case, the signal can simply be sent to a monitor to indicate the position of the instrument relative to the eye or other test object. In the former case, the signal is modified to treat the stored location as if it were the center of the CRT screen. In both cases, the signal sent to the CRT can also be evaluated electronically to verify that the instrument is correctly aligned before conducting a test.

A separate image tube or CCD array is used for a macro image of the eye, if desired. The macro optical system is designed to provide an image of the eye which appears sharp and uniformly illuminated. Illumination reflected from the eye by the alignment system is usually sufficient for the macro imaging system when the system of the preferred embodiment is utilized.

DESCRIPTION OF THE PREFERRED EMBODIMENTS

Figure 1:
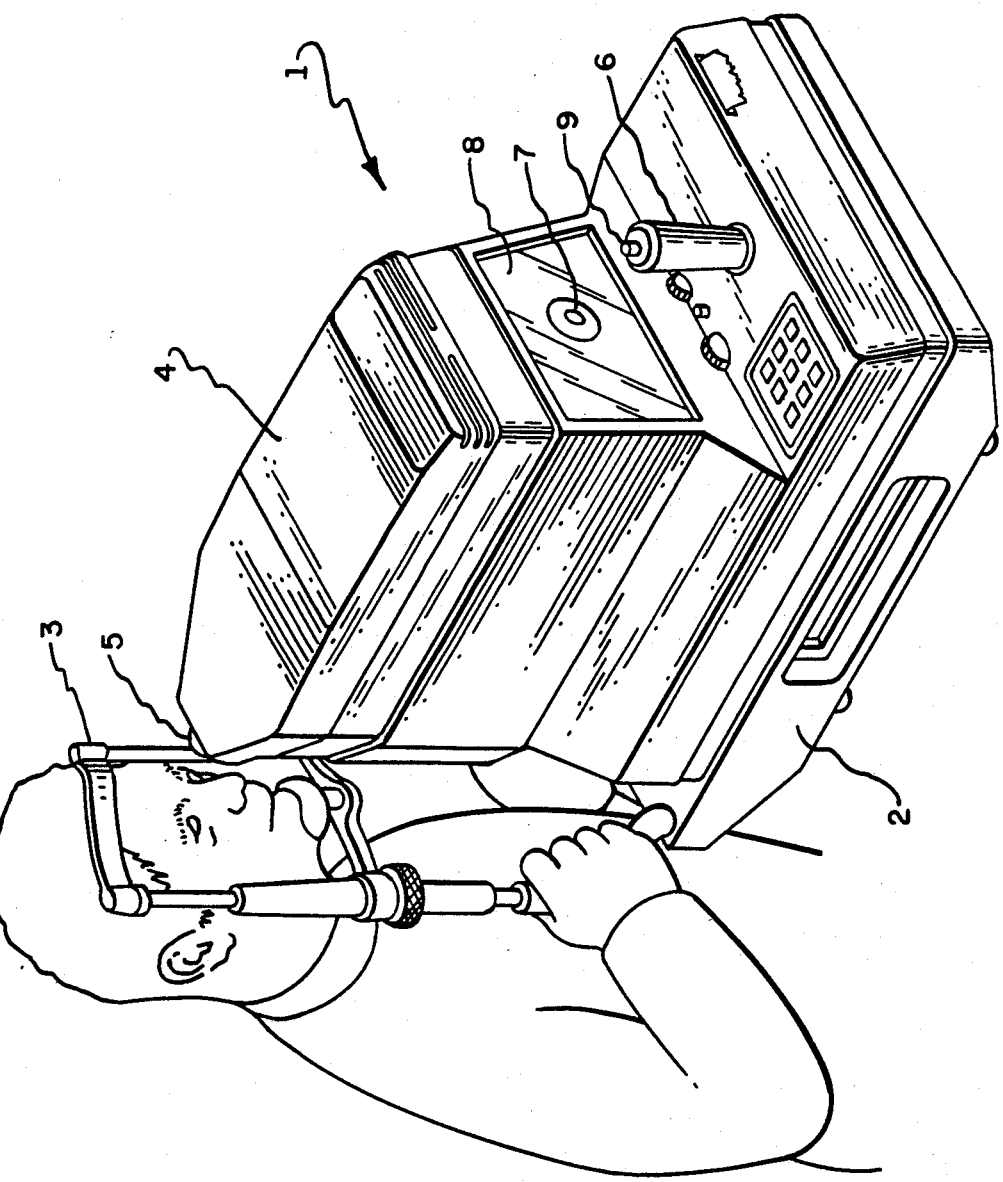
FIG. 1 is a perspective view of an ophthalmic instrument of a type suitable for use with the present invention.

Referring to FIG. 1, an ophthalmic instrument shown generally at 1, has a base 2 with a frame 3 to provide a steadying rest for the head of a patient. The test mechanism (not shown) of instrument 1 is contained within housing 4 movably mounted on base 2. Member 5 represents a portion of the instrument to be positioned in a predetermined relationship to the patient's eye. To accomplish this relationship, the operator uses joystick 6 to move housing 4 three dimensionally on base 2, while watching the resulting movement of symbols (not shown) relative to reticle 7 on screen 8. When the operator has achieved alignment by moving housing 4 until the symbols are contained within or superimposed on reticle 7, he presses button 9 on joystick 6 to initiate the desired test.

Figure 2:
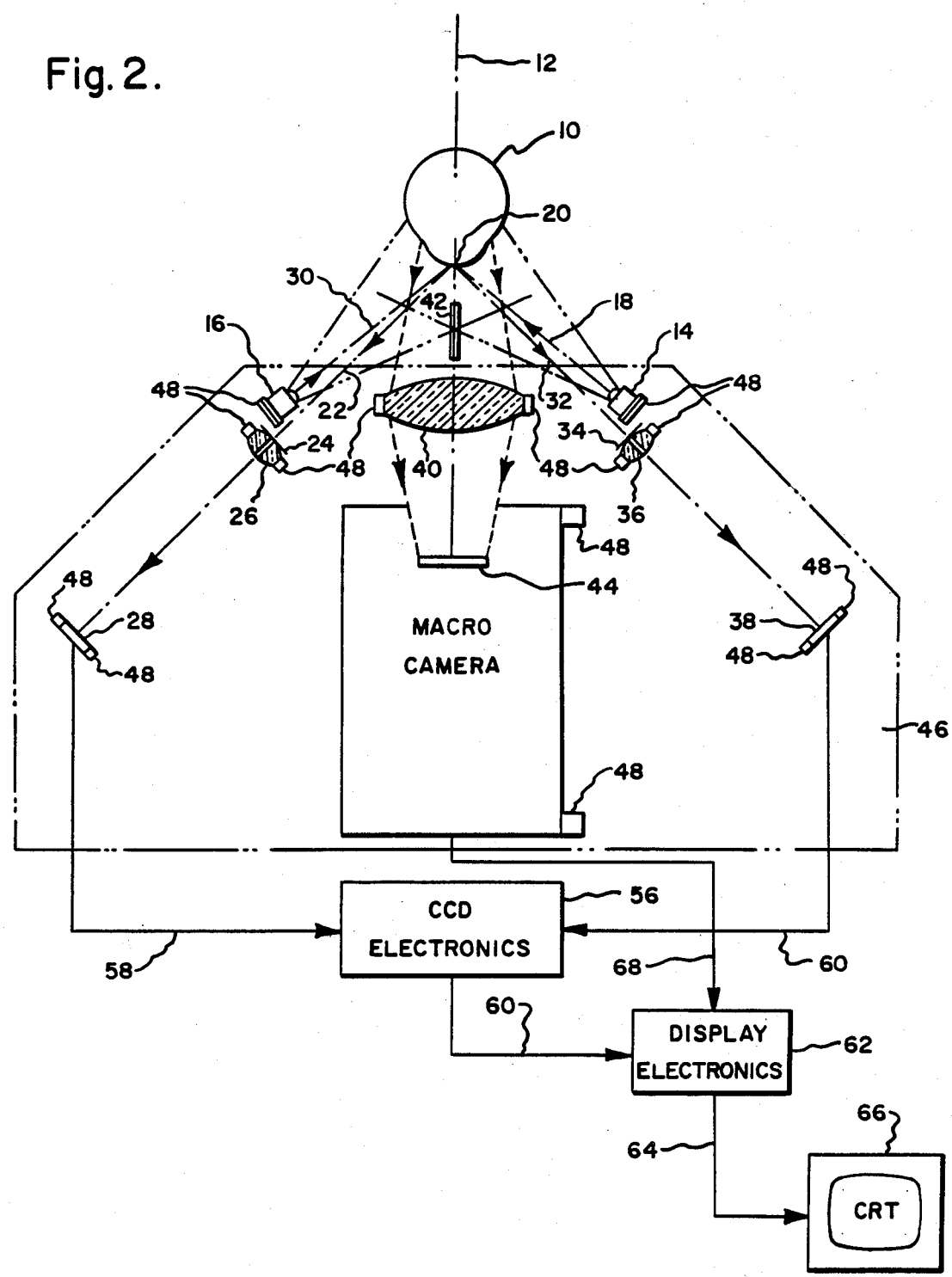
FIG. 2 is a diagrammatical view of a first embodiment of the present invention.

Referring to FIG. 2, eye 10 is flooded with light on one side of its axis 12 by light from source 14 and on the other side of its axis with light from source 16. Sources 14 and 16 may conveniently be LEDs emitting light in the infrared region. The advantage of infrared illumination resides in the insensitivity of the human eye to the infrared region. This avoids any discomfort, when high levels of radiation are required. Center ray 18 from source 14 is reflected from cornea vertex 20 along path 22 and sequentially through pinhole occluder 24, and lens 26 to CCD array 28. Similarly, center ray 30 of source 16 is reflected from cornea vertex 20 along path 32 and sequentially through pinhole occluder 34 and lens 36 to CCD array 38. A small bundle of rays closely adjacent to center rays 18 and 30 will remain substantially parallel thereto and pass along with the respective center ray through the respective pinhole occluder. A portion of the remaining light from each of sources 14 and 16 is reflected toward lens 40 to produce an image of eye 10 on video image detector 44. In the case of a non-contact tonometer, lens 40 is located behind air-pulse discharge tube 42.

The alignment system components may be conveniently mounted on plate 46 which has a plurality of mounting members 48 for holding sources 14 and 16; pinhole occluders 24 and 34; lenses 26 and 36; CCD arrays 28 and 38; objective lens 40 and video image detector 44. One advantage of the present invention which may be realized is that mounting members 48 do not require precise machining to close tolerances in order to provide exact angles and dimensions, since normal variations may be corrected electronically rather than optically. Electronic correction is achieved by positioning the instrument, containing the alignment system of the present invention, in the chosen relationship to the object such as a replica of a human eye. If the spot produced by occluders 24 and 34 is relatively close, e.g. <0.1 mm, to the center of the respective arrays, the XY location of the spot is conveniently stored in a device such as an EEROM. However, gross errors may be compensated for by moving the CCD to a new position in a plane normal to the respective paths 22 and 32. The reference locations (the locations of the respective spots on the CCD arrays) are thereafter considered to be the "center" of the respective CCD array.

Figure 3:
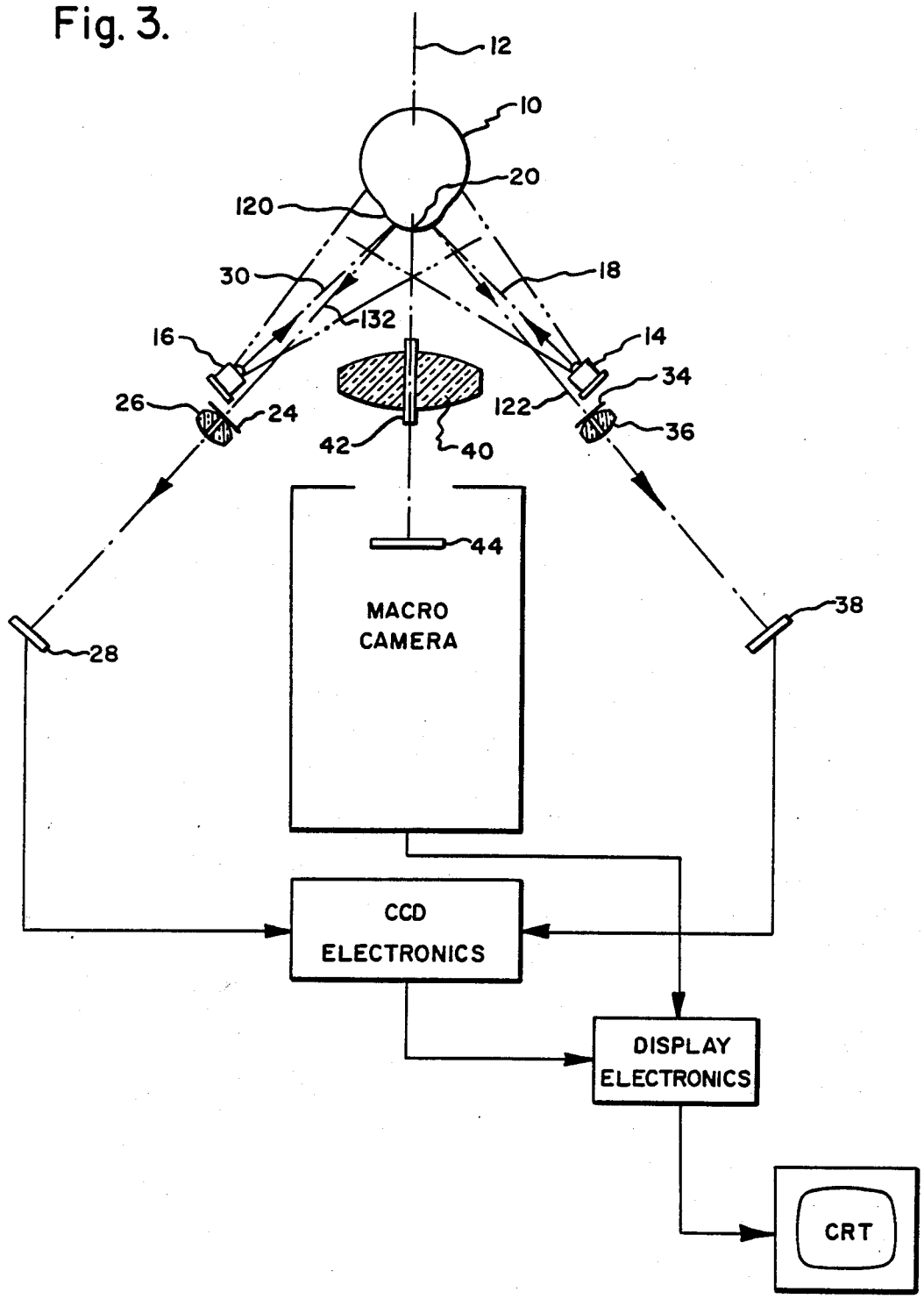
FIG. 3 is a diagrammatical view of a second embodiment of the present invention.

Referring now to FIG. 3, another embodiment of the present invention is illustrated. Light from sources 14 and 16 is reflected back from corneal surface 120 in the same general direction from which it came along paths 122 and 132, respectively to CCD arrays 28 and 38. In other respects, this embodiment operates in substantially the same manner as the embodiment of FIG. 2.

Figure 4:
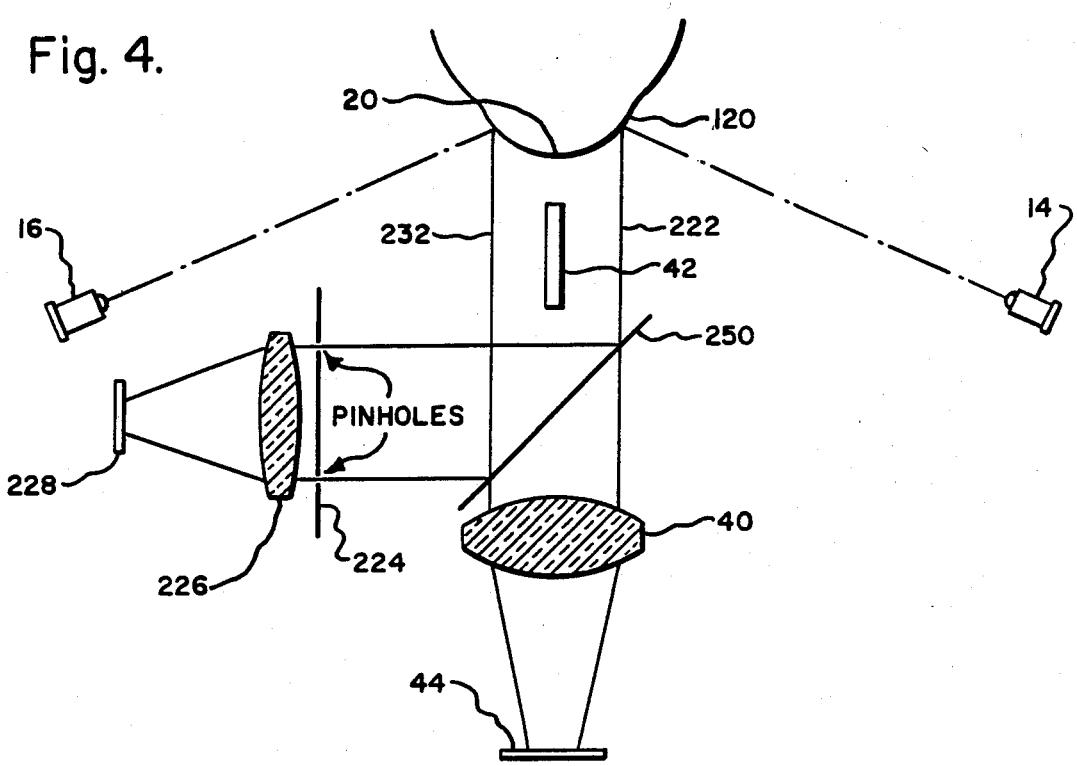
FIG. 4 is a diagrammatical view of a third embodiment of the present invention.

FIG. 4 illustrates still another embodiment. Light from sources 14 and 16 is reflected by the respective sides of cornea 120 along paths 222 and 232 toward objective 20. Beam splitter 250 diverts a portion of the light toward occluder 224 having two pinholes 252 and 254. Light passing through pinholes 252 and 254 is imaged by lens 226 on CCD array 228. In this embodiment, sources 14 and 16 are alternately strobed in order for CCD array 228 to identify which of sources 14 and 16 produced the spot being observed.

Referring again to FIG. 2, signals identifying the XY location of the spots on CCD arrays 28 and 38 are delivered to CCD evaluating electronics 56 by leads 58 and 60. Electronics 56 compares the reported XY position of the spot to the stored reference location for each CCD array. An output from electronics 56 representing the location of the spot relative to the reference location is provided to display electronics 62 which in turn drives CRT 66 through leads 64 to provide symbols on CRT 66. The signal from video image detector 44 is similarly provided to display electronics 62 through lead 68 in order to provide a macro image of the eye on CRT 66. The location of the spot on a CCD array can be identified conveniently using a raster sweep of the CCD pixel signals. The signal and location values of the first pixel are stored until a higher signal value is encountered during the sweep. Each time a higher signal value is encountered, the new pixel signal and location values are stored replacing the values previously stored until the sweep is complete. The location values stored at the end of the sweep identify the center of the spot on the respective CCD array. If a minimum signal threshold is set, artifacts, such as glare spots that can result from illumination for the macro view, are ignored by the system. When an optical system of the type illustrated by FIG. 4 is used, the timing of the raster sweep of CCD array 228 is synchronized with the strobe of sources 14 and 16 in order that even raster sweeps relate to one source and odd raster sweeps to the other.

Figure 5:
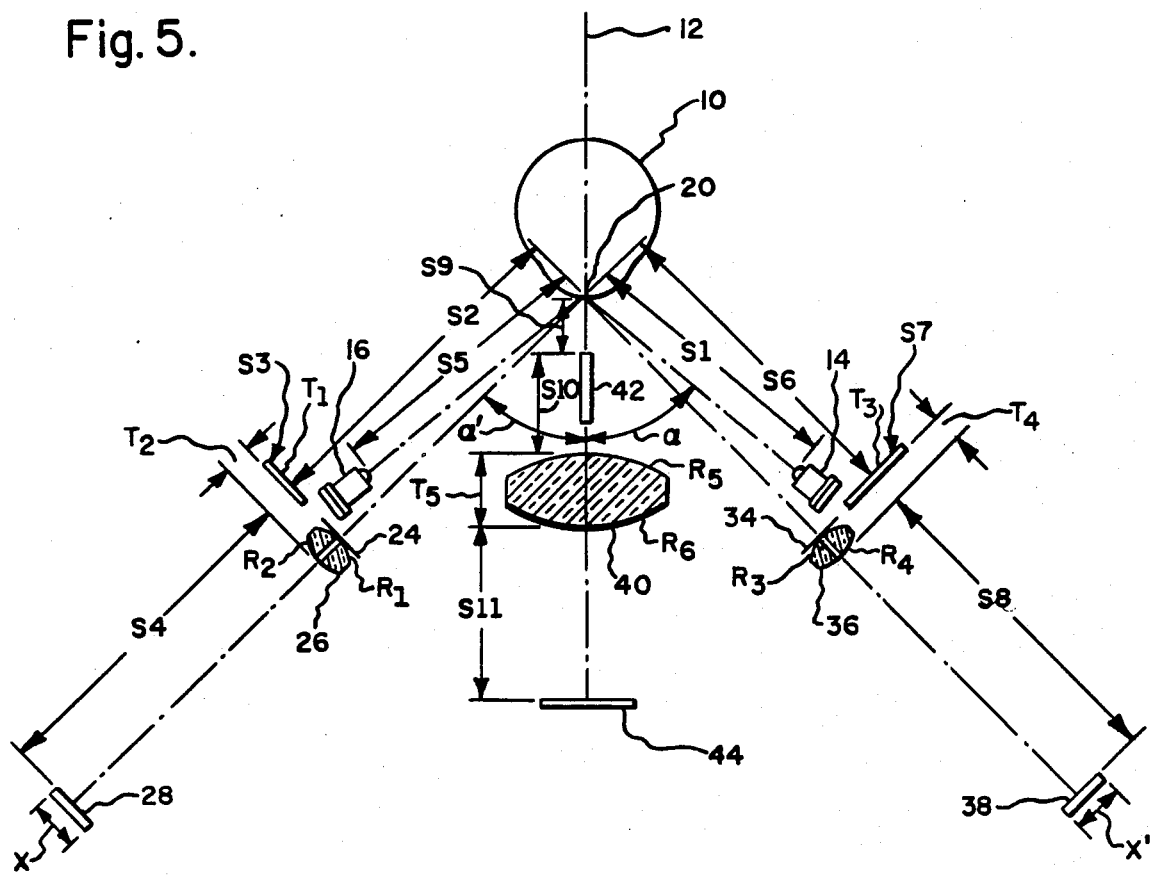
FIG. 5 is an optical diagram of the first embodiment of the present invention.

A preferred optical system according to FIG. 2 is diagrammatically presented in FIG. 5 and has the following values:

| Element | Radius | Thickness | Spacing | Index of Refraction |
|---|---|---|---|---|
| 14 | | | | |
| | | | S1 = 55.0 | |
| 20 | | | | |
| | | | S2 = 60.0 | |
| 24 | D1= 0.5 | T1 = 0.5 | | |
| | | | S3 = 0.5 | |
| | R1= 30.489 | | | |
| 26 | | T2 = 3.00 | | N1 = 1.5168 |
| | R2= −30.489 | | | |
| | | | S4 = 60.0 | |
| 28 | | | | |
| 16 | | | | |
| | | | S5 = 55.0 | |
| 20 | | | | |
| | | | S6 = 60.0 | |
| 34 | D2= 0.5 | T3 = 0.5 | | |
| | | | S7 = 0.5 | |
| | R3= 30.489 | | | |
| 36 | | T4 = 3.00 | | N2 = 1.5168 |
| | R4= −30.489. | | | |
| | | | S8 = 60.0 | |
| 38 | | | | |
| 20 | | | | |
| | | | S9 = 12.30 | |
| 42 | | | | |
| | | | S10 = 87.7 | |
| | R5= 50.813 | | | |
| 40 | | T5 = 5.00 | | N3 = 1.5168 |
| | R6= −50.813 | | | |
| | | | S11 = 100.0 | |
| 44 | | | | | wherein, radii, R1 to R6, thicknesses, T1 to T5, spacings, S1 to S11, pinhole diameters, D1 and D2, are in mm; radii having their center of curvature on the eye 10 side of the lens are indicated by a minus (−) sign; and indexes of refraction, N1 to N3, are absolute values. The pinhole-lens combinations can be replaced by small diameter lenses if desired. The model Texas Instruments TC211 CCD array is suitable for practicing this invention.

The amount of instrument movement necessary to obtain distance (S9) of object 10 from component 42 of the instrument being aligned can easily be calculated using the location value related to movement in a direction parallel to the plane containing the optical elements of the alignment system obtained from each CCD array. For example, if $\alpha=45°$ and $\alpha'=42°$ and x and x' are the relative locations in the directions indicated by the arrows labeled x and x' in FIG. 5, $\Delta S9=(x-X)-(x'-X')$, where X and X' are the reference locations for the respective CCD array. The amount of movement can be presented two dimensionally, for example on the CRT, by using one symbol for the horizontal (x) axis and another for the vertical (y) axis. The space between the symbols can be used to represent $\Delta S9$. When $\Delta S9=0$, the two symbols are superimposed. A simpler and more user-friendly procedure is the use of a cursor which moves above the screen center, if the instrument is too far from the object and below the screen center, if the instrument is too close. The cursor type of presentation is preferred because it has several advantages. One advantage is the ease with which the user can recognize whether the instrument is too close or too far away. Another advantage is that the x and y positions can be displayed by means that do not require superimposition of symbols to indicate correct positioning. For example, a narrow vertical line can be used to represent the relative horizonal position and a narrow horizontal line to indicate the relative vertical position, while the cursor indicates the relative distance from the object. Prior art alignment systems did not permit a choice of display formats.

Figure 6:
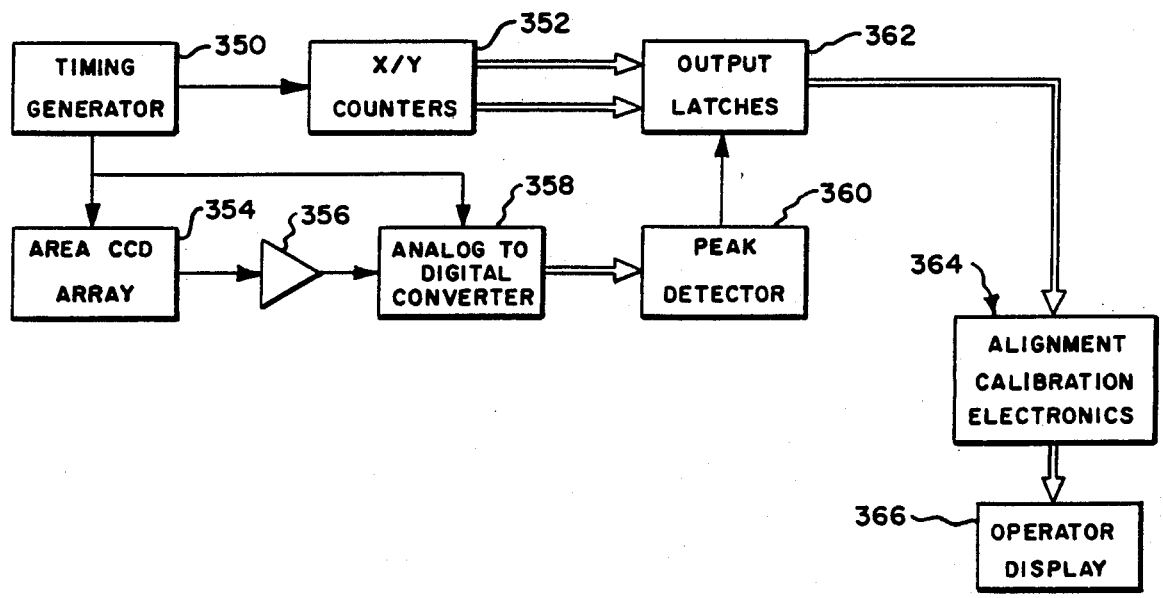
FIGS. 6 and 7 are block diagrams for explaining electronics supporting the present invention.
Figure 7:
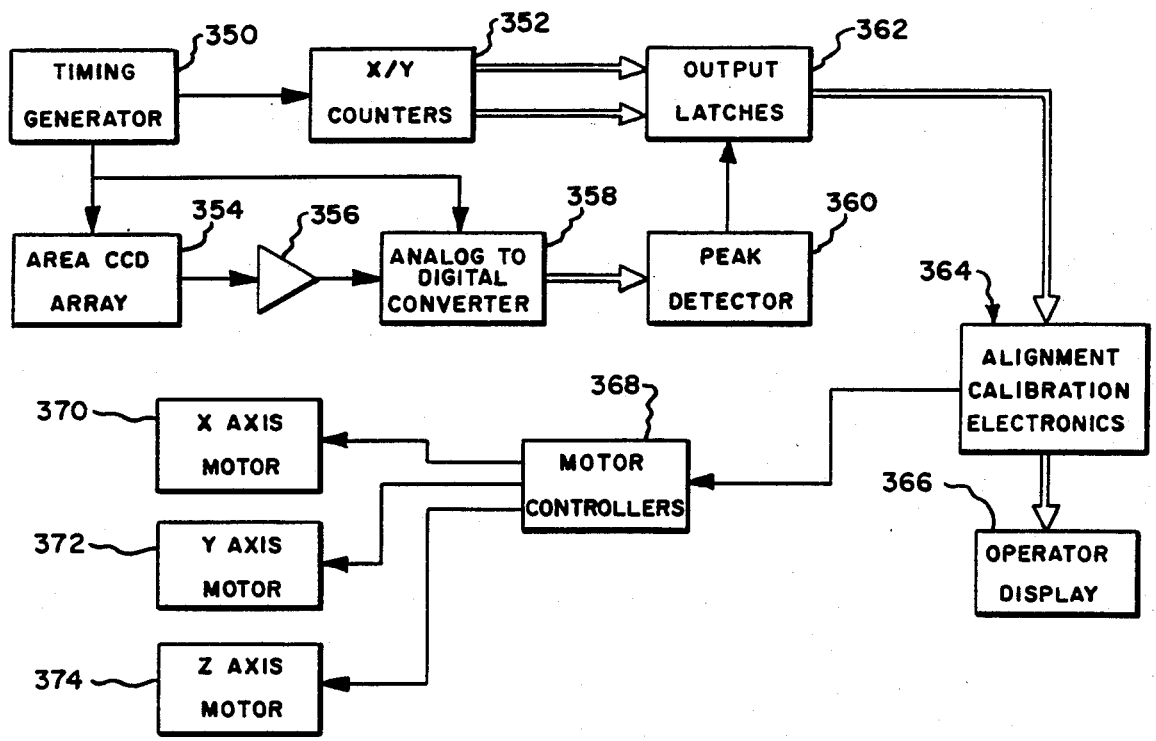

Referring now to FIG. 6, signals from timing generator 350 drive x/y counters 352, the raster sweep of CCD array 354 and timing of A/D converter 358. Each pixel signal is amplified by amplifier 356, sent to A/D converter 358, whose output is evaluated by peak detector 360. The outputs of x/y counters 352 are stored by latches 362, each time peak detector 360 signals a new high for the pixel signals from CCD array 354. Obviously, each array requires an amplifier, A/D converter, peak detector and output latches. The outputs of latches 362 are evaluated at the end of each raster sweep by alignment and calibration electronics 364 which updates operator display 366. If an automatic alignment system is desired, motor controllers 368 and motors 370, 372 and 374 can be added as shown in FIG. 7. The value of $\Delta z$ is determined as explained previously for the determination of $\Delta S9$, $$\text{while } \Delta x = \frac{(x - X) + (x' - X')}{2} \text{ and}$$

$$\Delta y = \frac{(y - Y) + (y' - Y')}{2}$$

These $\Delta$ values are provided to motor controllers 368 by alignment and calibration electronics 364 to position the system until all three $\Delta$'s=0.

What is claimed is:

1. An alignment system for an ophthalmic instrument comprising,
   (a) illuminating means for illuminating an eye with diverging rays from a light source,
   (b) a first detecting means for defining a first light detecting area, said light detecting means including a first pinhole occluder to pass a small bundle of reflected rays producing a first signal identifying the XY location of reflected light on said first area,
   (c) a second detecting means for defining a second light detecting area, said second detecting means including a second pinhole occluder to pass a small bundle of reflected rays and producing a second signal identifying the XY location of reflected light on said second area,
   (d) means evaluating said first and second signals for providing a third signal, and
   (e) means for selectively positioning the instrument relative to the eye responsive to said third signal.

2. The alignment system according to claim 1, wherein said positioning means includes manually operated means for moving the instrument and display means for presenting a visual indication of the instrument position.

3. The alignment system according to claim 2, wherein said illumination means includes two light paths, one of said two paths directing light toward an eye from one side and the other of said two paths directing toward the eye from the other side.

4. The alignment system according to claim 3, wherein said first detecting means is impinged by reflected light from said first light path and said second detecting means is impinged by reflected light from said second light path.

5. The alignment system according to claim 1, wherein each of said first and second detecting means includes a positive lens adjacent said pinhole occluder.

6. The alignment system according to claim 2, further including electro-optical means for producing a fourth signal representing a macro image of the eye.

7. The alignment system according to claim 1, wherein said evaluating means includes storage means for retaining information representing first and second reference locations on said first and second areas respectively, said reference locations symbolizing first and second locations impinged by reflected light when the instrument is positioned at a chosen position relative to an eye and said third signal includes a comparison of said first and second signals with said information.

8. The alignment system according to claim 7, wherein said positioning means includes manually operated means for moving the instrument and display means for presenting a visual indication of the instrument position.

9. The alignment system according to claim 8, wherein said illumination means includes two light paths, one of said two paths directing light toward an eye from one side and the other of said two paths directing toward the eye from the other side.

10. The alignment system according to claim 9, wherein said first detecting means is impinged by reflected light from said first light path and said second detecting means is impinged by reflected light from said second light path.

11. The alignment system according to claim 10, wherein each of said first and second detecting means includes a positive lens adjacent said pinhole occluder.

12. The alignment system according to claim 11, further including electro-optical means for producing a fourth signal representing a macro image of the eye.

13. The alignment system according to claim 11, wherein said first detecting means is located on said other side and said second detecting means is located on said one side.

14. The alignment system according to claim 1, wherein said positioning means includes electromechanical means for moving the instrument.

15. The alignment system according to claim 14, wherein said illumination means includes two light paths, one of said two paths directing light toward an eye from one side and the other of said two paths directing toward the eye from the other side.

16. The alignment system according to claim 15, wherein said first detecting means is impinged by reflected light from said first light path and said second detecting means is impinged by reflected light from said second light path.

17. The alignment system according to claim 16, wherein said first detecting means is located on said other side and said second detecting means is located on said one side.

18. The alignment system according to claim 17, wherein each of said first and second detecting means includes a positive lens adjacent said pinhole occluder.

19. The alignment system according to claim 18, wherein further including display means for presenting a visual indication of the instrument position.

20. The alignment system according to claim 19, further including electro-optical means for producing a fourth signal representing a macro image of the eye.

21. The alignment system according to claim 20, wherein said evaluating means includes storage means for retaining information representing first and second reference locations on said first and second areas respectively, said reference locations symbolizing first and second locations impinged by reflected light when the instrument is positioned at a chosen position relative to an eye and said third signal includes a comparison of said first and second signals with said information.

22. The alignment system according to claim 16, wherein said first detecting means is located on said one side and said second detecting means is located on said other side.

23. An alignment system for an ophthalmic instrument comprising,
 (a) first illuminating means for providing light having rays from a source diverging to an eye from one side thereof,
 (b) second illuminating means for providing light having rays from a source diverging to an eye from the other side thereof,
 (c) detecting means for defining an area, said light detecting means including an occluder having two spaced pinholes to pass two small bundles of reflected rays, one of said bundles comprising rays from said first illuminating means and the other of said bundles comprising rays from the second of said illuminating means for producing first and second signals identifying the XY location of reflected light passing through each of said pinholes on said area,
 (d) means evaluating said signals for providing an output signal, and
 (e) means for selectively positioning the instrument relative to the eye responsive to said output signal.

24. The alignment system according to claim 23, wherein said detecting means includes a positive lens adjacent said occluder.

25. The alignment system according to claim 24, further including electro-optical means for producing a video signal representing a macro image of the eye.

26. The alignment system according to claim 24, wherein said positioning means includes manually operated means for moving the instrument and display means for presenting a visual indication of the instrument position.

27. The alignment system according to claim 26, further including beamsplitter means for producing a macro image of the eye using a portion of the light from at least one of said first and second illuminating means.

* * * * *